(12) United States Patent
Heinzerling et al.

(10) Patent No.: US 7,214,215 B2
(45) Date of Patent: May 8, 2007

(54) PUNCTURE DEVICE WITH A FLEXIBLE CATHETER TUBE FOR CONNECTING TO A MEDICAL INFUSION LINE

(75) Inventors: Jörg Heinzerling, Bad Hersfeld (DE); Simone Bölinger, Mönchengladbach (DE); Roland Csincsura, Eisenach (DE)

(73) Assignee: Clinico GmbH, Hersfeld (DE)

( * ) Notice: Subject to any disclaimer, the term of this patent is extended or adjusted under 35 U.S.C. 154(b) by 0 days.

(21) Appl. No.: 11/182,250

(22) Filed: Jul. 15, 2005

(65) Prior Publication Data

US 2006/0015076 A1    Jan. 19, 2006

(30) Foreign Application Priority Data

Jul. 15, 2004    (EP) .................................. 04016627

(51) Int. Cl.
*A61M 5/00* (2006.01)
(52) U.S. Cl. .................................... 604/264; 604/93.01
(58) Field of Classification Search ................ 604/264, 604/164.01, 158, 198, 523, 263, 192, 93, 604/272, 533, 890.1, 93.01; 606/185, 213; 285/197
See application file for complete search history.

(56) References Cited

U.S. PATENT DOCUMENTS

| | | | |
|---|---|---|---|
| 5,514,117 A * | 5/1996 | Lynn .......................... 604/536 |
| 5,545,143 A * | 8/1996 | Fischell ....................... 604/180 |
| 5,713,872 A | 2/1998 | Feuerborn | |
| 5,735,818 A * | 4/1998 | Kriesel et al. .............. 604/132 |
| 5,858,005 A * | 1/1999 | Kriesel ......................... 604/180 |
| 5,971,963 A * | 10/1999 | Choi ........................... 604/177 |
| 6,056,718 A * | 5/2000 | Funderburk et al. ...... 604/93.01 |
| 2004/0044318 A1* | 3/2004 | Fiser et al. ................. 604/263 |

\* cited by examiner

*Primary Examiner*—Nicholas Lucchesi
*Assistant Examiner*—Christopher D. Koharski
(74) *Attorney, Agent, or Firm*—Friedrich Kueffner

(57) ABSTRACT

A puncture device with a flexible catheter tube for connecting to a medical infusion line, wherein the device includes a catheter connecting piece or hub attachable at the puncture site on the skin surface of a patient, wherein the catheter hub has a connector for connecting the infusion line and an outlet for the flexible catheter tube; and a needle holder having a puncture needle (stylet), wherein the flexible catheter tube is arranged in the interior of the catheter hub and extends out of the outlet with an output end. The end of the flexible catheter tube opposing the output end is located in the interior of the catheter hub in the area of the connector and is separated from the surrounding area by a septum, wherein the needle holder securely fastens the puncture needle insertable into a passage channel of the catheter tube at the end opposing the pointed or sharp puncture tip. The outlet is located at the bottom side of the catheter hub resting on the surface of the patient in the position of use and the puncture needle is made without a duct.

10 Claims, 5 Drawing Sheets

# PUNCTURE DEVICE WITH A FLEXIBLE CATHETER TUBE FOR CONNECTING TO A MEDICAL INFUSION LINE

The present application claims priority under 35 U.S.C. 119 of EP 04 016 627.4, filed Jul. 15, 2004, the entire disclosure of which is incorporated herein by reference.

BACKGROUND OF THE INVENTION

1. Field of the Invention

The present invention relates to a puncture device with a flexible catheter tube for connecting to a medical infusion line. The device includes a catheter connecting piece or hub attachable at the puncture site on the skin surface of a patient, wherein the catheter hub has a connector for connecting the infusion line and an outlet for the flexible catheter tube; and a needle holder having a puncture needle (stylet), wherein the flexible catheter tube is arranged in the interior of the catheter hub and extends out of the outlet with an output end. The end of the flexible catheter tube opposing the output end is located in the interior of the catheter hub in the area of the connector and is separated from the surrounding area by a septum, wherein the needle holder securely fastens the puncture needle insertable into a passage channel of the catheter tube at the end opposing the pointed or sharp puncture tip. The needle holder is detachably arranged at the connector of the catheter hub in a starting position of the puncture device such that the puncture needle penetrates the septum and is guided in the passage channel of the catheter tube past the output end.

2. Description of Related Art

In medicine, catheters are used in various fields for administering drugs which have been dissolved or suspended in fluid. Using catheters medication can be directly administered into the patient's tissue or bloodstream via a puncture site. In order to attach the catheter it is necessary to create an entry into the tissue or bloodstream of the patient by means of a puncture. Various puncture devices are known for this purpose. Puncture devices of the type described above are especially intended for independent use by the patient, for example, for administering insulin with the aid of an insulin pump.

Aside from known puncture devices with a flexible catheter tube, other comparable products exist which feature a hollow needle made of steel or of a comparable metal rather than a tube with which medication is administered.

For puncture devices with a flexible catheter tube and a puncture needle, when the catheter hub is attached to the skin surface of the patient, the underlying tissue is pierced by the puncture needle, while the flexible catheter tube is inserted into the tissue in the process. The patient's stomach area is frequently chosen as the incision site for the puncture device. Following insertion, the puncture needle is withdrawn and removed. Only the catheter tube remains in the puncture site, wherein the catheter tube has previously been hooked up to an infusion line attached to the catheter hub and therefore, to medication delivery.

In a type of known puncture devices such as those described above, the outlet is located at the bottom side of the catheter hub which rests on the skin of the patient in the position of use, while an input end opposite the output end of the flexible catheter tube and the end thereof opposing the sharp or pointed tip of a puncture needle, extend out of the catheter hub at different openings. Both of these openings are sealed off by means of a septum with respect to the surrounding area.

A puncture device of the above-described type is distributed by the company Disetronic Medical Systems AG, in Burgdorf, Switzerland under the name "Disetronic®Tender". The outlet for the flexible catheter tube in this puncture device is located at the side of the catheter hub. A hollow needle used as a puncture needle and securely fastened in a needle holder extends within the catheter tube which is guided through the interior of the catheter hub. The needle extends for the most part in a straight line and exits the catheter hub nearly horizontally at its side. For attaching the catheter, the patient—based on visual judgment—must first insert the puncture needle with the protruding end of the catheter tube at an angle of 30° to 45° into the skin, then pull the needle backwards out of the catheter tube, twist the catheter connector by 30° to 45° and finally secure it flatly to the skin. In doing so, the section of flexible catheter tube now located inside the body is also bent.

Although an additional septum is not necessary for this puncture device, the same problem arises as with puncture devices of the aforementioned type, namely that prior to insertion of such a puncture device the free volume of the catheter tube must either be vented or flooded with the medication to be administered. For this purpose, the hollow needle which is inserted into the septum and through to the output end of the catheter tube for creating a puncture must exhibit a laterally arranged vent hole or grinding, so that venting can be effected by way of the needle cavity or passageway. Since hollow needles are limited in minimal diameter by the fact that the needle cavity or passageway is passable by a fluid and the material surrounding the cavity is strong enough so as not to break, the minimal external diameter of the catheter tube is inevitably confined to a larger diameter than that of the guided hollow needle used for puncturing. Due to the subsequent, relatively large catheter tube size (in this case external diameters of 0.5 to 0.7 mm are common) the catheter tubes are perceived as uncomfortable or even painful by patients. Upon removal of the catheter, these puncture devices also leave behind wounds which are larger in diameter and thus, heal slower and are associated with a higher infection risk.

Consequently, the puncture devices of the aforementioned type are not as widely accepted by patients as desired or possible in spite of their otherwise existing advantages compared to puncture devices having a hard hollow needle made of metal (for example, no problems with nickel intolerance, no stiff needle which could cause pain when abutting the catheter). Moreover, the additional required step of venting makes attaching and handling the puncture device especially difficult for a patient when inserting it himself and gives way to risks caused by incorrect handling.

The puncture device known as Disetronic®Tender is especially complicated to handle (the angle choice) and there is a danger that incorrect operation or handling (a too large angle) can kink the output end of the catheter tube, thereby blocking the medication flow or even breaking the hollow needle used as a puncture needle in the body of the patient.

SUMMARY OF THE INVENTION

Therefore, it is the primary object of the present invention to improve the puncture device of the aforementioned type such that the catheter tube has a smaller external diameter compared to known catheter tubes and handling is simplified.

In accordance with the invention, this object is met by a puncture device of the aforementioned type in which the outlet is located at the bottom side of the catheter hub resting on the surface of the patient in the position of use and the puncture needle is made without a duct.

Thus, according to the present invention, the puncture needle which extends the entire length of the catheter tube to the connector where the flexible catheter tube ends, and from there through the septum with which the rear connection of the flexible catheter tube is sealed off from the surrounding area, is made without a duct and thereby differs from the known state of the art. In this manner, the puncture needle fills out the interior of the flexible catheter tube in the starting position. There is no additional space left for an air bubble which would necessitate venting or flooding. After puncturing the puncture needle can be withdrawn axially from the catheter tube and the catheter hub. By means of the resulting negative pressure and suction effect, the flexible catheter tube automatically fills almost completely with body fluid (lymph, blood). A separate step of venting or flooding the hollow puncture needle can be omitted. The puncture needle can be made, for example, of solid material in a sandwich construction or with single-sided or doubled-sided closed ends and thereby has a significantly smaller external diameter. As a result, the external diameter of the catheter tube can be reduced, for example to a diameter of 0.4 mm or smaller. Aside from the reduced external diameter of the catheter tube and the no longer required separate venting step, a further advantage of the present invention results from the fact that a septum can be omitted compared to some puncture devices known from the prior art. Moreover, the smaller external diameter of the catheter tube results in a significantly reduced tube volume initially filled with body fluid upon insertion the puncture device and which then must be displaced when applying an infusion line (for example a tube from or to an insulin pump), thereby adulterating the initial dose of especially small dosages. Finally, a needle without a duct is less expensive to manufacture than a hollow needle which requires an additional grinding or bore in its inner duct for discharging air. An increase of the inner diameter of the catheter tube also ultimately leads to a smaller area for cell growth and therefore to longer stay intervals compared to the aforementioned configuration with a hollow steel needle.

Moreover, since the outlet is located at the bottom side of the catheter hub, the puncture device can be easily handled by the patient. The patient only has to place it on the skin surface and then press in order to puncture without observing an insertion angle.

Of course, the flexible catheter tube according to the invention can certainly have a larger diameter if necessary; depending on the area of application, the catheter tube protruding from the catheter hub can also be made in different lengths in order to penetrate various tissue layers.

The flexible catheter tube is preferably made of plastic without being limited to this type of material. Other flexible materials are also conceivable. Of course, when selecting a material, its compatibility must be taken into account.

In accordance with an advantageous embodiment of the present invention, the catheter hub is essentially flat and the catheter tube protrudes diagonally to the plane of the essentially flat catheter hub at the bottom side of the catheter hub out of the outlet, and is curved and guided in the plane within the interior of the catheter hub, and the connector is aligned with the end of the catheter tube opposite the output end.

This essentially flat design of the puncture device is especially advantageous for puncture devices used for example by insulin patients on a daily basis. Since these patients should be able to move about freely with an inserted puncture device and attached infusion line, an essentially flat catheter hub is far less bothersome since it is less susceptible to being caught in clothing. Bumping into a protruding catheter hub on the one hand can be painful, and on the other hand can lead to a dislodging of the catheter hub and the catheter tube as a consequence, such that only a new insertion could guarantee the administering of medication. In this embodiment of the puncture device, the puncture needle extending the length of the catheter tube in the starting position of the catheter configuration is naturally bent corresponding to curvature of the catheter tube. Possible angles of the output end of the catheter tube relative to the catheter hub range between 0° and 90°, whereas angles of 30° and more are preferred.

In accordance with another embodiment, the needle holder of the puncture device includes a rigid front section attached to the connector in the starting position, and a rigid back section in which the end opposite the puncture tip of the puncture needle is securely attached, and a flexible middle section connecting both sections. The flexible section is composed of two legs located at a distance from each other and flexibly connected to the rigid sections, preferably by means of film hinges, wherein the legs are curved outwardly in the starting position, such that the front section and back section have a minimal distance from each other. This provides the advantage that after puncturing and attaching the catheter hub, the puncture needle can be pulled out of the catheter tube in a safe and easy manner. Simply by taking hold and pulling on the back section of the needle holder, a force is exerted on the puncture needle axially parallel to the centerline of the flexible catheter tube. This force effects the withdrawal of the puncture needle from the catheter tube without wielding lateral pressures which could lead to a shifting or detaching of the catheter tube in the puncture site. After withdrawing the puncture needle from the catheter tube, the needle holder can be separated from the connector of the catheter hub, removed and discarded.

In order to provide better handling when detaching the needle holder, the needle holder is preferably equipped with a gripping handle.

Once the puncture needle has been removed from the interior of the catheter tube, the septum seals off the lumen in the interior of the catheter tube from external influences until the connecting piece of an infusion line equipped with an appropriate element such as a needle, pierces the septum and administers a flow of medication dissolved or suspended in fluid.

In the event that the puncture device described above is additionally designed such that the legs have locking devices with which they can be locked against each other in a straightened position, wherein the front section and the back section exhibit a maximal distance from each other, and as a result are secured in this position. The puncture needle is withdrawn from the interior of the catheter tube by straightening the legs of the flexible section of the needle holder and securing them against each with a locking action, whereby subsequent penetration of the puncture needle into the flexible catheter tube is prevented. In this manner the puncture needle remains in a retracted position, so as not to present a danger for the patient or other persons during the disposal of the needle holder.

In an effort to eliminate danger caused by the puncture needle once the needle holder has been removed from the catheter hub, the puncture device is preferably designed such that the longitudinal measurements of the puncture needle and of the sections of the needle holder are selected so that the puncture tip of the puncture needle is located within the needle holder when the legs are straightened. According to this embodiment, the puncture needle is positioned with its puncture tip inside the needle holder after use, so that the danger of being pricked (always connected with an infection hazard) is eliminated for patients or third parties.

Designed for easily connecting an infusion line to the catheter tube, the septum is preferably pre-perforated.

In order to ensure that the catheter hub remains safely secured to the skin surface of the patient, the connector preferably has a self-adhesive layer on a bottom side. This can be, for example, an adhesive film applied to cellulose which is covered by a protective film prior to the use of the catheter.

Finally, the puncture device in its original sealed packaging preferably has a protective cap which covers the output end of the catheter tube as well as the puncture tip of the puncture needle in an originally sealed condition. The protective cap prevents injuries inflicted by an unintentional prick of the puncturing needle prior to use and continues to warrant a sterile catheter tube.

A double curvature of the catheter tube is beneficial for fastening the catheter tube in the catheter hub by means of for example insert molding or gluing. Moreover, this curvature (in principle characterized as s-shaped) of the catheter tube reduces the gliding forces resulting from the withdrawal of the puncture needle initially extending the catheter tube and thereby prevents the breaking of the needle.

An additional advantageous embodiment of the puncture device according to the present invention resides in the fact that the wall of the catheter tube at its output end is rounded or flattened in the direction of the puncture tip of the puncture needle. There is therefore no abrupt edge which could cause the patient pain when puncturing or inserting the catheter tube. Rounding or flattening can result for example by pressing the end of the cannula onto the puncture needle.

DETAILED DESCRIPTION OF THE PREFERRED EMBODIMENTS

Figure 1:
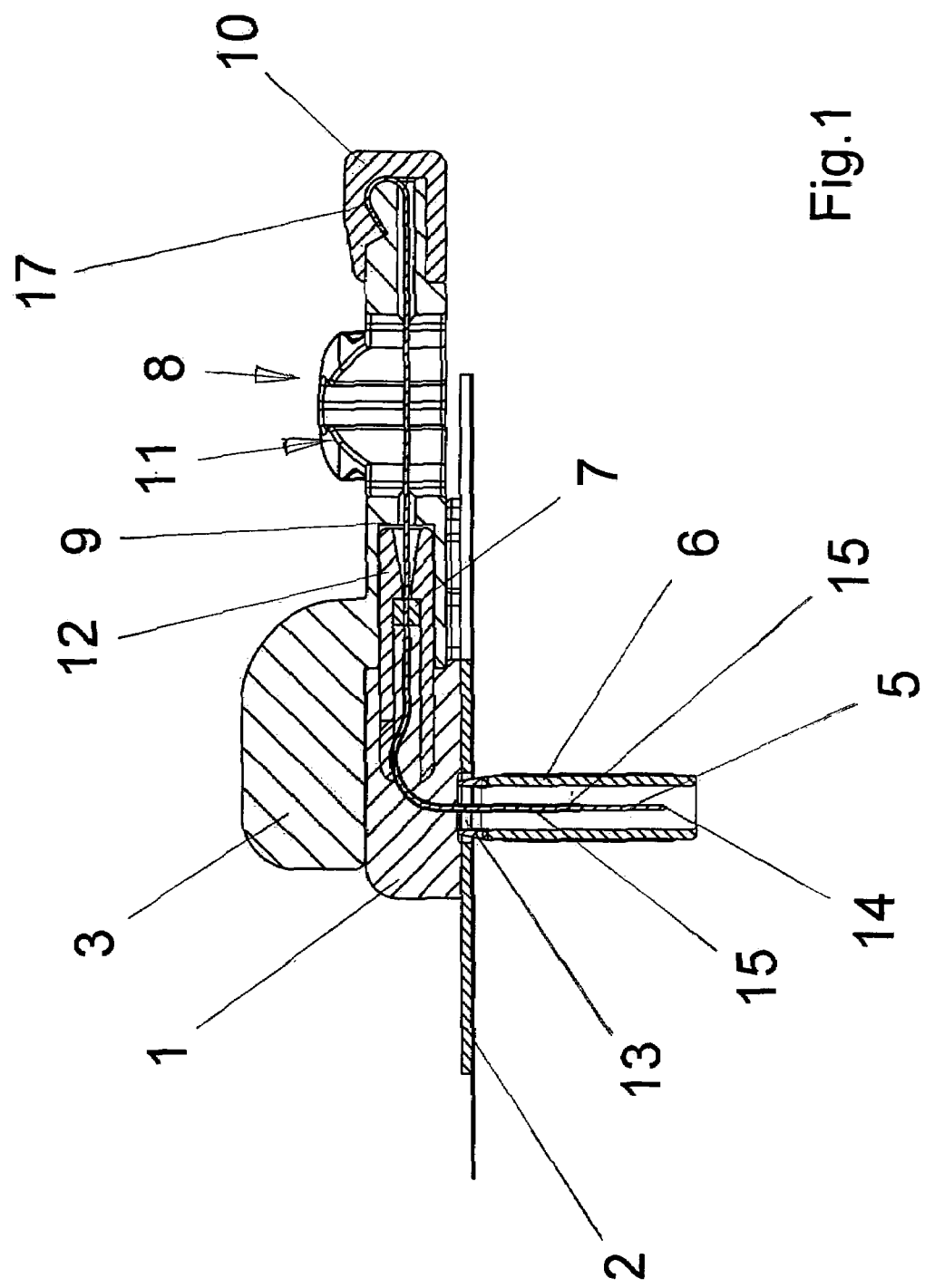
FIG. 1 is a cross-sectional side view of a puncture device according to the present invention in the starting position.
Figure 2:
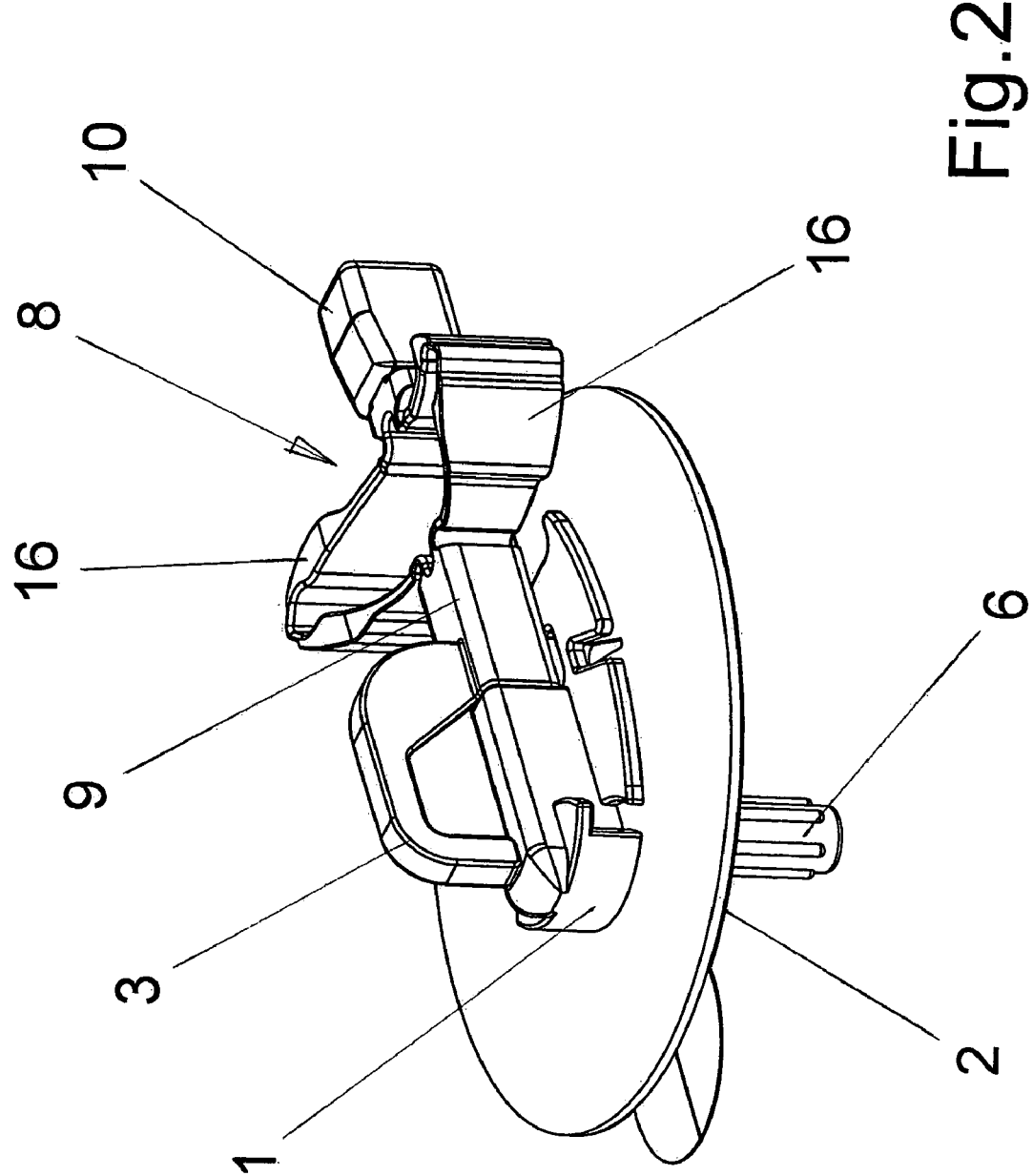
FIG. 2 is a three-dimensional view diagonally from above showing the puncture device according to FIG. 1.
Figure 3:
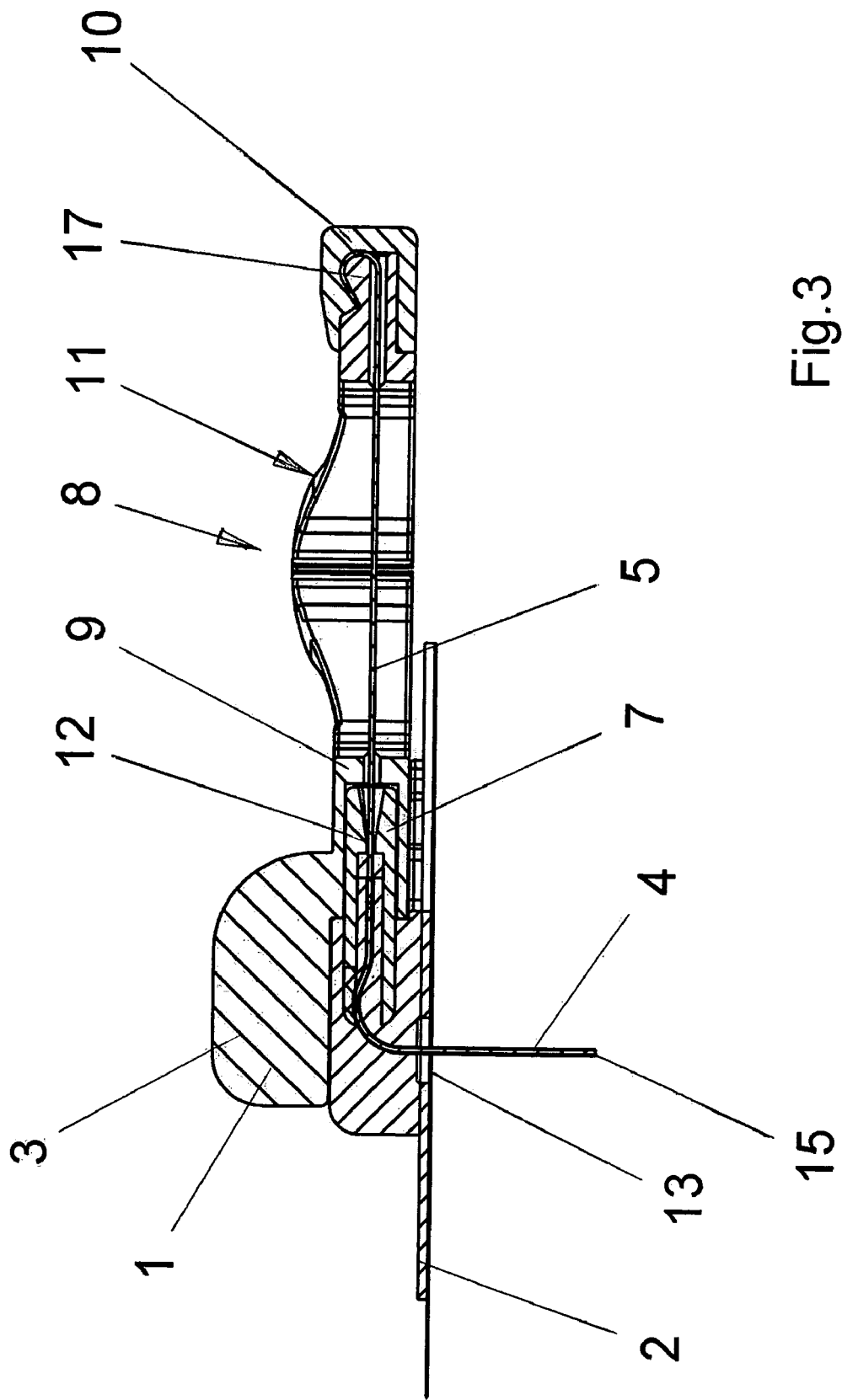
FIG. 3 is a cross-sectional side view of the puncture device according to FIG. 1 after puncture and the withdrawal of the puncture needle.
Figure 4:
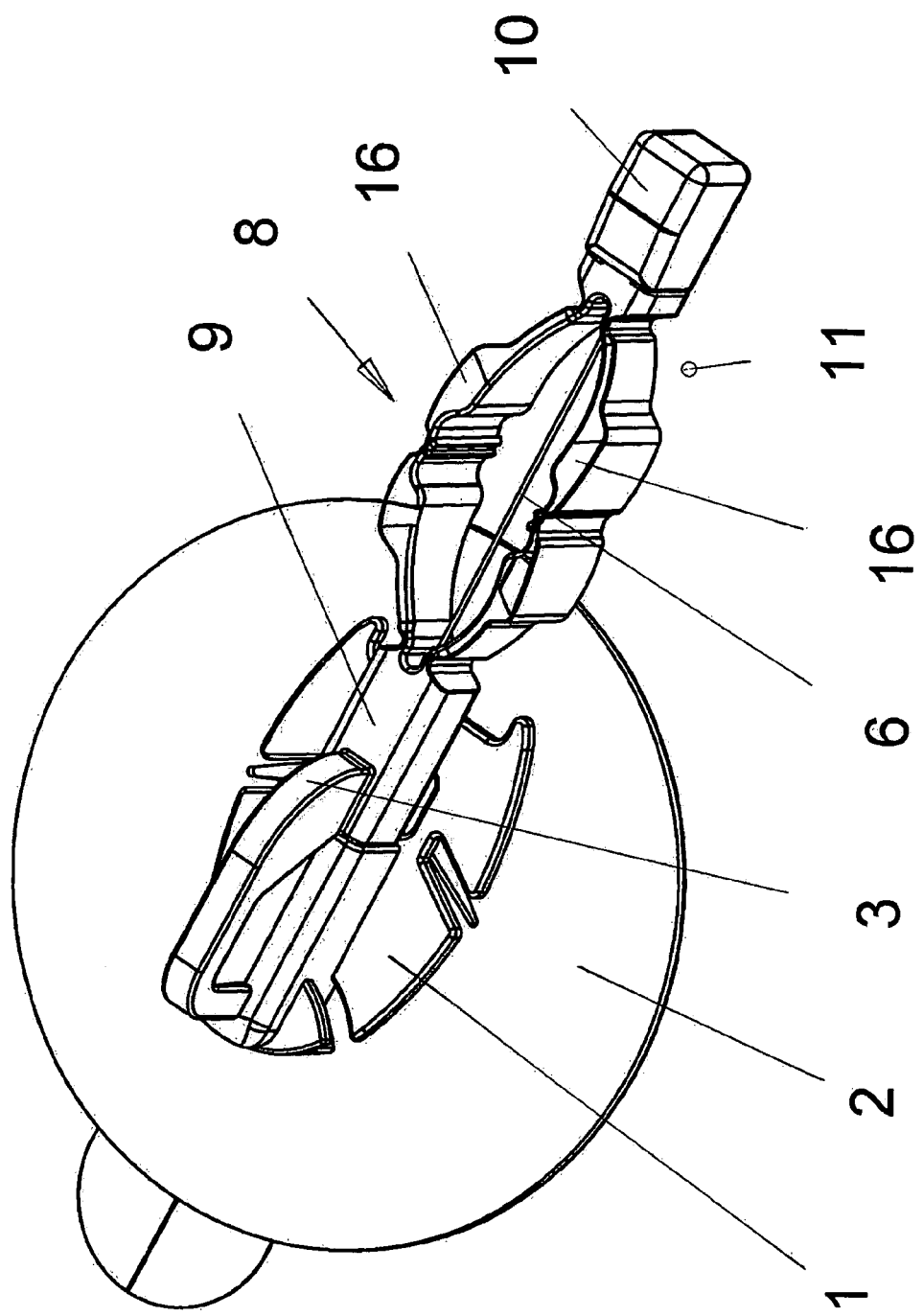
FIG. 4 is a three-dimensional view diagonally from above showing the puncture device according to FIG. 1.
Figure 5:
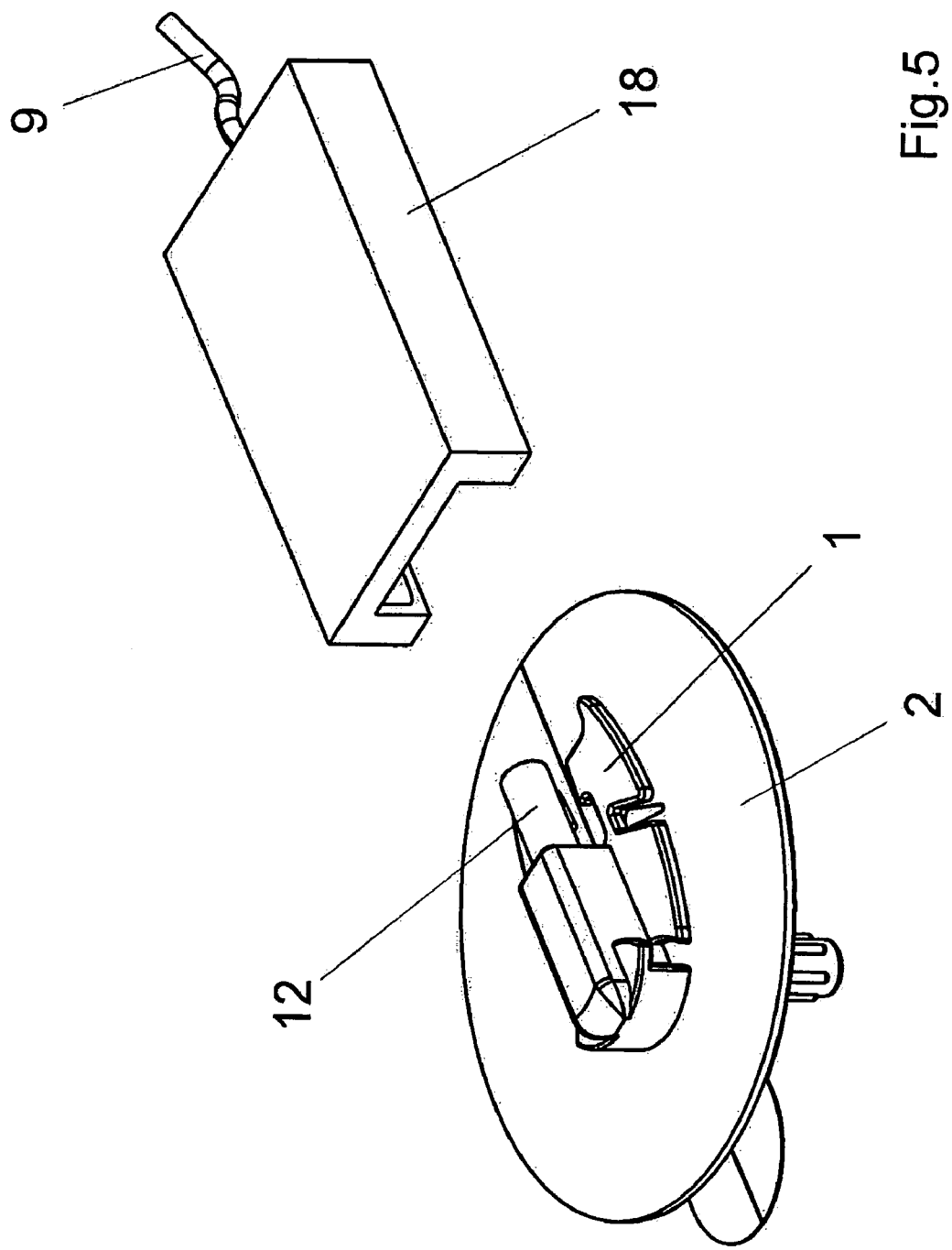
FIG. 5 is a three-dimensional view diagonally from above, showing the catheter hub of puncture device after detaching the needle holder, a connector for an infusion line as well as a schematically illustrated connecting piece of an infusion line ready for connection.

FIGS. 1 through 5 show a model of a puncture device according to the present invention from different views and in different positions of use. FIGS. 1 and 2 show the puncture device in a starting position prior to a puncture. FIGS. 3 and 4 show the puncture device in a position following the puncture and the withdrawal of the puncture needle from the catheter tube. Finally, FIG. 5 shows the catheter hub after the removal of the needle holder together with the connecting piece of an infusion line ready for connection.

The puncture device is basically composed of two parts, a catheter hub1 and a needle holder 8. The catheter hub 1 is essentially flat in design. The catheter hub 1 has an adhesive disk 2 with a self-adhesive film fitted on the bottom side thereof which is covered with a protective film in the starting position as shown in FIGS. 1 and 2. The catheter hub 1 also has a connector 12 by means which the catheter hub is connectable to an infusion line. The connector 12 essentially has a cylindrical exterior and is aligned with its centerline parallel to the plane of the catheter hub 1. A flexible catheter tube 4 is positioned essentially vertically to the flat extension of the catheter hub 1 and is led out of an outlet 13 located at the bottom side of the catheter hub 1 in the position of use. A puncture needle 5 runs along the hollow interior of the catheter tube 4 in the starting position and projects out of the said tube with a pointed or sharp puncture tip 14 at the output end 15 of the catheter tube 4. In the starting position this area is covered with a protective cap 6 in order to prevent injuries and bacterial contamination of the puncture needle 5 and the catheter tube 4. The catheter tube 4 is led into the body of the catheter hub 1 and is there diverted by way of a double curvature (following a sort of s-shape) by approximately 90° to then be guided essentially axially along the centerline of the connector 12 into the connector and to the end thereof. The catheter tube 4 ends in a septum7 arranged inside of the connector 12. The double curvature mainly serves to reduce the gliding forces arising during the withdrawal of the puncture needle 5 from the catheter tube 4.

In the starting position the needle holder 8 is attached to the connector 12 of the catheter hub 1 with a rigid front section 9. The needle holder 8 has a gripping handle 3 at its rigid front section 9. Next to the rigid front section 9 the needle holder 8 has a rigid back section 10 located opposite the rigid front section as well as a flexible middle section 11 which connects both rigid sections 9 and 10. As illustrated in FIG. 2, the middle section 11 of the needle holder 8 is composed of two legs 16 which are movable about film hinges in themselves and relative to the front and back sections 9 and 10. In the starting position shown in FIGS. 1 and 2 the legs 16 are spread and folded, so that the front section 9 and the back section 10 of the needle holder 8 are axially adjoined. The puncture needle 5 is fixed with its back end 17 opposite the puncture tip 14 in the back section 10 of the needle holder 8. Thus, in the starting position the puncture needle 5 is in its maximally advanced position in the catheter tube 4, wherein the puncture tip 14 protrudes beyond the output end 15 of the catheter tube 4. The puncture needle 5 is thereby led through the septum 7 which seals the catheter tube 4 at the connector 12 relative to the surrounding area. In this manner, the puncture device according to the present invention manages with only one septum 7. The puncture needle 5 runs along the interior of the catheter tube 4 and is curved in the area of the catheter hub 1 corresponding to the curvature of the catheter tube 4. In the needle holder 8 the puncture needle 5 extends essentially aligned to the back section of the catheter tube 4 which faces the connector 12.

Prior to inserting the puncture device the patient must remove the protective cap 6 and peel off the protective film of the adhesive disk 2. The patient then presses the puncture device vertically onto the site of his body to be punctured, whereby the puncture needle 5 penetrates through the skin into the underlying tissue while simultaneously creating space for the penetrating catheter tube 4. For this action, the patient should grasp and hold the puncture device by its gripping handle 3.

Once the puncture device is applied to the body, the puncture site pierced and the catheter hub 1 affixed by means of the adhesive disk 2 in this manner, the patient must remove the puncturing needle 5 from the catheter tube 4. For this purpose the legs 16 of the middle section 11 of the needle holder 8 are pressed together from their initial spread position in the starting position (FIG. 2), whereby the back section 10 disconnects itself from the front section 9 of the needle holder 8 (see FIGS. 3 and 4). The puncture needle 10 which is securely attached with its back end 17 in the back section 10 of the needle holder 8 is thereby gradually pulled out of the catheter tube 4 in the direction of the connector 12 through the septum 7. The thereby resulting vacuum in the interior of the catheter tube 4 effects that body fluid (blood, lymph) infiltrates the output end and is sucked in. By means of locking devices, not shown in detail, positioned at the legs 16, the legs can be locked against each other in an extended position in order to prevent that the puncture needle 5 again penetrates the catheter tube 4. The catheter tube 4 is now freely passable and almost completely flooded with body fluid due to the above-described vacuum. A separate flooding or venting of the catheter tube 4, as required by known puncture devices from the state of art, can be omitted. The needle holder 8 is designed in its longitudinal extension such that when the legs 16 are extended, the puncture needle 5 rests with its puncture tip 14 protected in the interior of the front section 9 of the needle holder 8. By pulling on the gripping handle 3, the needle holder 8 can be loosened and disconnected from the connector 12 and then safely disposed of.

The situation as shown in FIG. 5 results from the above, wherein the catheter hub 1 with its connector 12 is standing by for the connection of a connecting piece 18 of an infusion line 19. The catheter tube 4 is securely positioned in the tissue of the patient; its duct is flooded and open for the infusion of medication.

It is concluded from the preceding description of the model arrangement that the puncture device according to the present invention provides the desired advantages by means of a special guidance of the puncture needle 5 in the interior of the catheter tube 4, along the entire length thereof and out of the catheter hub 1 through the septum 7. Also, the septum 7 can be pre-perforated. Compared to other known models, the catheter tube can have a diameter distinctly smaller; a separate flooding or venting of the catheter tube 4 prior to actual insertion is not required; and the handling of this puncture device is in general simplified.

We claim:

1. A puncture device comprising a flexible catheter tube f or connecting to a medical infusion line having a catheter hub attachable at a puncture site on the skin surface of a patient, and having a connector for connecting the infusion line and an outlet for the flexible catheter tube, and a needle holder having a puncture needle, wherein the flexible catheter tube is arranged in an interior of the catheter hub and extends out through the outlet with its output end, wherein the end of the flexible catheter tube opposite the output end is located in the interior of the catheter hub in the area of the connector and separated from the surrounding area by a septum, and wherein the needle holder securely fastens the puncture needle insertable into a passage channel of the catheter tube at the end opposite the pointed or sharp puncture tip, and is detachably arranged at the connector in a starting position of the puncture device such that the puncture needle penetrates the septum and is guided in the passage channel of the catheter tube beyond the output end, wherein the outlet is arranged on a bottom side of the catheter hub resting on the patient surface in the position of use, and in wherein the puncture needle is made without a duct, wherein the catheter hub is essentially flat, wherein the catheter tube protrudes diagonally to the plane of the essentially flat catheter hub at the bottom side of the catheter hub out of the outlet, and is curved and guided in the plane within the interior of the catheter hub, and the connector is aligned with an end of the catheter tube opposite the output end.

2. A puncture device according to claim 1, wherein the needle holder comprises a rigid front section attached to the connector in the starting position, a rigid back section in which the end opposite the puncture tip of the puncture needle is securely attached, and a flexible middle section connecting said sections, wherein the flexible section is comprised of two legs located at a distance from each other and flexibly connected to the rigid sections, wherein the legs are curved outwardly in the starting position, such that the front section and back section have a minimal distance from each other.

3. A puncture device according to claim 2, wherein the flexible connection is comprised of film hinges.

4. The puncture device according to claim 3, wherein the longitudinal measurements of the puncture needle and of the sections of the needle holder are selected such that the puncture tip of the puncture needle is located within the needle holder when the legs are straightened.

5. The puncture device according to claim 2, wherein the legs are lockable against each other in a straightened position, wherein the front section and the back section have a maximum distance from each other, and as a result are secured in this position.

6. The puncture device according to claim 1, wherein the needle holder has a gripping handle.

7. The puncture device according to claim 1, wherein the septum is pre-perforated.

8. The puncture device according to claim 1, wherein the catheter hub has a self-adhesive layer located at a bottom side intended for attaching to the skin surface of the patient.

9. The puncture device according to claim 1, wherein a protective cap covers the output end of the catheter tube as well as the puncture tip of the puncture needle in an originally sealed condition.

10. The puncture device according to claim 1, wherein the catheter tube curves twice in opposite curving directions so as to change its direction in the interior of the catheter hub.

* * * * *